United States Patent [19]

Crivello et al.

[11] 4,450,360
[45] * May 22, 1984

[54] ALKYLARYLIODONIUM SALTS AND METHOD FOR MAKING

[75] Inventors: James V. Crivello, Clifton Park; Julia L. Lee, Schenectady, both of N.Y.

[73] Assignee: General Electric Company, Schenectady, N.Y.

[*] Notice: The portion of the term of this patent subsequent to Aug. 16, 2000 has been disclaimed.

[21] Appl. No.: 357,435

[22] Filed: Mar. 12, 1982

[51] Int. Cl.$^3$ .............................................. C07F 9/66
[52] U.S. Cl. ................................... 260/440; 260/446; 568/8; 568/13; 430/917; 430/468; 430/464
[58] Field of Search ................... 260/440, 446; 568/8, 568/13

[56] References Cited

U.S. PATENT DOCUMENTS 3,981,897  9/1976  Crivello ............................. 260/440
4,238,394 12/1980  Crivello et al. ................. 260/446 X
4,238,619 12/1980  Crivello et al. ................. 260/446 X
4,329,300  5/1982  Crivello et al. ................. 260/446 X

OTHER PUBLICATIONS

[Hydroxy(tosyloxy)iodo]benzene, a Versatile Reagent for the Mild Oxidation of Aryl Iodides at the Iodine Atom by Ligand Transfer, Koser et al., J. Org. Chem, 45, 1542–1543, (1980).
New Type of Iodonium Salt, Nieland et al., Russian Polytechnical Institute. Translated from Zhurnal Organicheskoi Chimii, vol. 6, No. 4, pp. 885–886, 4/70. Original Articles Submitted 6/9/69.
Hypervalent Organoiodine. Crystal Structure of Phenylhydroxytosyloxyiodine, Koser et al., J. Org. Chem., vol. 41, No. 22, (1976).
Hypervalent Organoiodine. Reactions of Silver Arylsulfonates with Iodosobenzene Dichloride, Koser et al., J. Org. Chem., vol. 42, No. 8, (1977).
Iodonium Ylides, Reactions of Phenyldimedonyliodone with Several Thiocarbonyl Compounds. Evidence of Sulfur Ylide Intermediates, Koser et al., J. Org. Chem., vol. 41, No. 1, (1976).

Primary Examiner—Helen M. S. Sneed
Attorney, Agent, or Firm—William A. Teoli; James C. Davis, Jr.; James Magee, Jr.

[57] ABSTRACT

Arylalkyliodonium salts are provided which can be used as thermal or photoinitiators for polymerization of a wide variety of cationically polymerizable organic materials. Reaction is effected between an aryliodonium tosylate and an active hydrogen aliphatic organic compound, such as dimedone, to produce an intermediate arylalkyliodonium tosylate salt which is thereafter reacted with a polyfluoro metal or metalloid salt of an alkali or alkaline earth metal to produce the desired arylalkyliodonium polyfluoro metal or metalloid salt, such as dimedonylphenyliodonium hexafluoroarsenate.

10 Claims, No Drawings

ALKYLARYLIODONIUM SALTS AND METHOD FOR MAKING

CROSS REFERENCE TO RELATED APPLICATIONS

Reference is made to our copending application Ser. No. 357,433 for Method for Making Diaryliodonium Salts, filed concurrently herewith and assigned to the same assignee as the present invention.

BACKGROUND OF THE INVENTION

Prior to the present invention, as shown by Crivello, U.S. Pat. No. 3,981,897, certain diarylhalonium salts were prepared by initially forming an intermediate diarylhalonium bisulfate, and thereafter the diarylhalonium bisulfate was reacted with a hexafluoro compound, such as a Group Va hexafluoride salt, for example, sodium hexafluorophosphate, potassium hexafluoroantimonate or potassium hexafluoroarsenate. The resulting diaryliodonium hexafluoro metal or metalloid salts were found to be useful as photoinitiators for a wide variety of cationically polymerizable organic materials, such as epoxy resins.

As shown by Nielands and Karele, Journal of Organic Chemistry, U.S.S.R. 6, 889 (1970) alkylaryliodonium salts were synthesized by condensing dimedone and dimedone ethylether with [hydroxy(tosyloxy)iodo]benzene.

The [hydroxy(tosylate)iodo]benzene was prepared by the reaction of the corresponding iodosobenzene diacetate with a $C_{(1-13)}$ organic sulfonic acid, for example, a strong alkyl or aryl sulfonic acid, such as benzenesulfonic acid, 3-nitrobenzenesulfonic acid, 3-chlorobenzenesulfonic acid, trifluoromethanesulfonic acid, methanesulfonic acid, p-toluenesulfonic acid, etc.

We have now discovered that the aforementioned reaction of Nielands and Karele can be applied to a variety of aliphatic compounds in addition to dimedone to produce a wide variety of arylalkyliodonium tosylate salts. In addition, we have also found that a wide variety of arylalkyliodonium salts exhibiting valuable properties such as thermal initiators, and photoinitiators for various cationic polymerizable organic materials, for example, epoxy resins can be made by a straight forward metathesis between the arylalkyliodonium tosylate and polyfluoro metalloid salt in accordance with the following equation:

$$[RIY]^+[QSO_3]^- + XMF_d \rightarrow [RIY]^+[MF_d]^- + QSO_3X,$$

where R is a $C_{(6-13)}$ aryl radical, Y is a monovalent aliphatic or cycloaliphatic group selected from

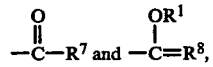

$R^1$ and $R^4$ are selected from hydrogen and $C_{(1-8)}$ alkyl, $R^2$ and $R^3$ are

or a mixture of

where $R^7$ and $R^8$ are selected from $C_{(1-13)}$ organic radicals which together can form a member selected from a $C_{(6-13)}$ aromatic structure, $C_{(5-13)}$ heterocyclic structure, two $C_{(6-13)}$ aryl radicals, a mixture of $C_{(1-8)}$ alkyl radical and a $C_{(6-13)}$ aryl radical, and a mixture of alkyl and oxyalkyl, or alkyl and oxyaryl, and $R^5$ and $R^6$ are monovalent electron withdrawing groups selected from nitrile and a mixture of nitro and $C_{(6-13)}$ aryl, Q is a $C_{(1-13)}$ organic radical, X is an ion selected from hydrogen, alkali metals and alkaline earth metals, M is a metal or metalloid selected from antimony, arsenic, phosphorus and boron, and d is an integer equal to from 4–6 inclusive.

Statement of the Invention

An arylalkyliodonium salt having the formula, $$[R-I-Y]^+MF_d^- \tag{1}$$

where R, Y, M and d are as previously defined.

There are included within the arylalkyliodonium salts of formula (1) compounds having the formula,

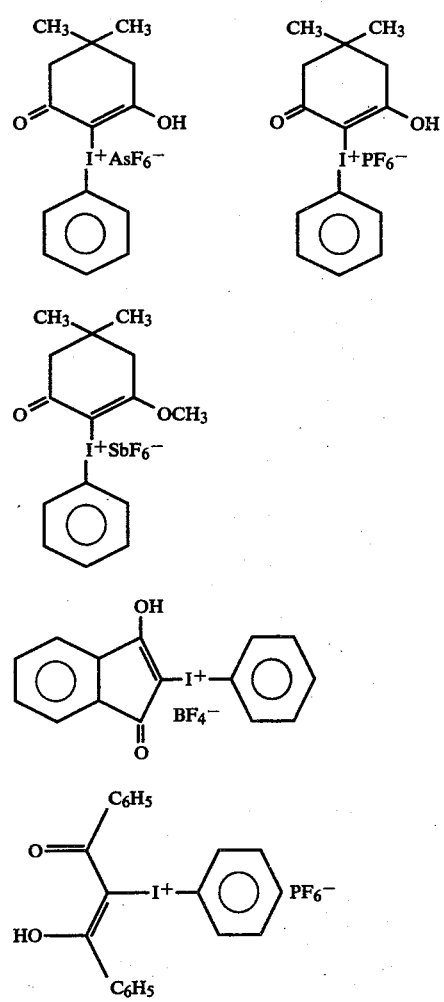

-continued

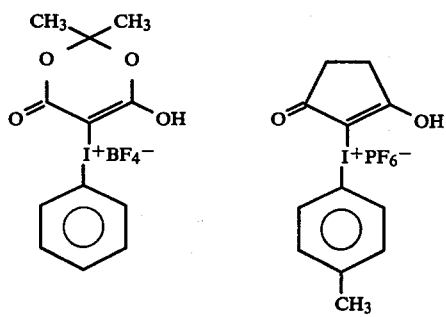

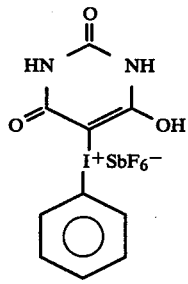

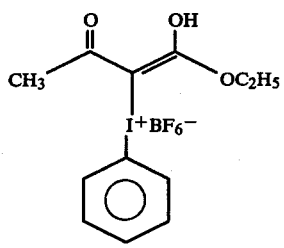

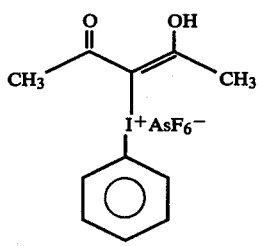

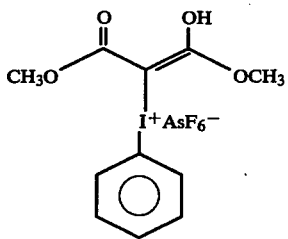

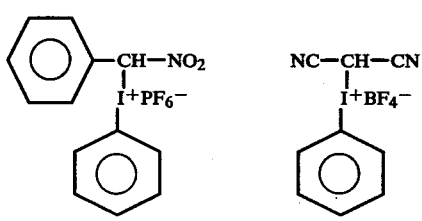

-continued

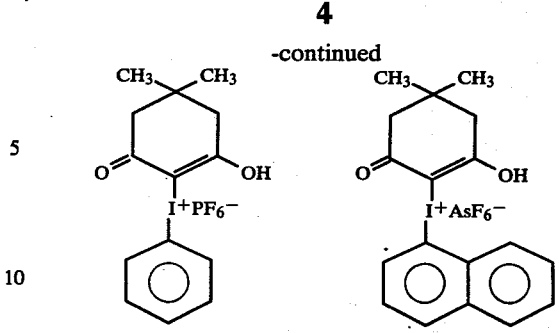

As previously shown, the alkylaryliodonium salts of the present invention can be made by effecting the condensation of an active hydrogen compound with a [hydroxy(tosyloxy)iodo] aromatic compound to produce an intermediate alkylaryliodo tosylate, followed by the reaction of the intermediate alkylaryliodonium tosylate salts with a alkali metal or alkaline earth metal Group Va metal or metalloid salt or corresponding acid. Included by the Group Va metal polyfluoride acids and salts are hexafluoride salts, such as $NaPF_6$, $NaAsF_6$, $KSbF_6$, $KAsF_6$, $Ca(PF_6)_2$, $Mg(AsF_6)_2$, $HPF_6$, $HAsF_6$, $HSbF_6$, $Ba(AsF_6)_2$, $Pb(PF_6)_2$, $Zn(AsF_6)_2$, etc.

Among the active hydrogen compounds which can be used in the practice of the present invention to make the alkylaryliodonium polyfluoro metal salts are compounds such as

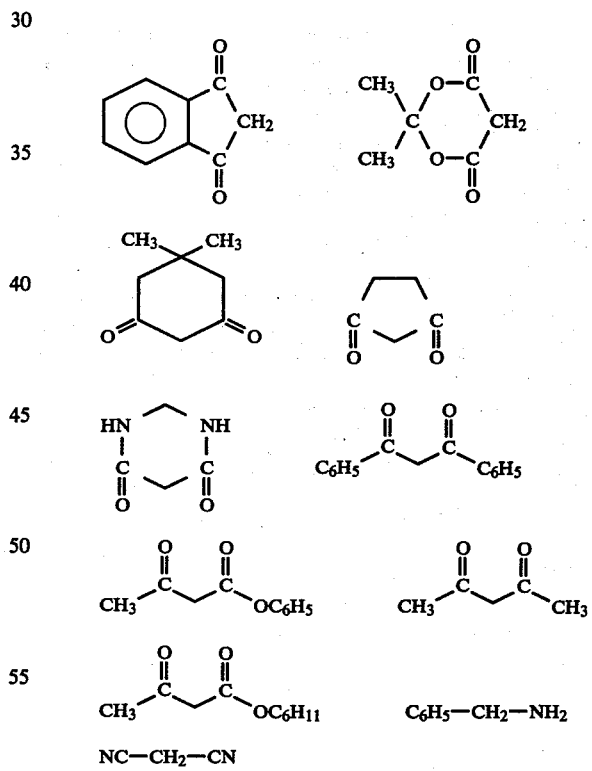

NC—CH₂—CN

The alkylaryliodonium salts of the present invention can be used as thermal or photoinitiators for a wide variety of cationically polymerizable organic materials among which are epoxy resins.

The term "epoxy resin" as utilized in the description of the cationically polymerizable compositions of the present invention, includes any monomeric, dimeric or oligomeric or polymeric epoxy material containing one or a plurality of epoxy functional groups. For example, those resins which result from the reaction of bisphenol-A (4,4′-isopropylidenediphenol) and epichlorohydrin, or by the reaction of low molecular weight phenolformaldehyde resin (Novolak resin) with epichlorohydrin, can be used alone or in combination with an epoxy containing compound as a reactive diluent. Such diluents as phenyl glycidyl ether, 4-vinylcyclohexene dioxide, limonene dioxide, 1,2-cyclohexene oxide, glycidyl acrylate, glycidyl methacrylate, styrene oxide, allyl glycidyl ether, etc., may be added as viscosity modifying agents.

In addition, the range of these compounds can be extended to include polymeric materials containing terminal or pendant epoxy groups. Examples of these compounds are vinyl copolymers containing glycidyl acrylate or methacrylate as one of the comonomers. Other classes of epoxy containing polymers amenable to cure using the above catalysts are epoxy-siloxane resins, epoxy-polyurethanes and epoxy-polyesters. Such polymers usually have epoxy functional groups at the ends of their chains. Epoxy-siloxane resins and method for making are more particularly shown by E. P. Pluedemann and G. Fanger, J. Am. Chem. Soc., 80, 632-5, (1959). As described in the literature, epoxy resins can also be modified in a number of standard ways such as reaction with amines, carboxylic acids, thiols, phenols, alcohols, etc., as shown in U.S. Pat. Nos. 2,935,488; 3,235,620; 3,369,055; 3,379,653; 3,398,211; 3,403,199; 3,563,840; 3,567,797; 3,677,995; etc. Further coreactants which can be used with epoxy resins are hydroxy terminated flexibilizers such as hydroxy terminated polyesters, shown in the Encyclopedia of Polymer Science and Technology, Vol. 6, 1967, Interscience Publishers, New York, pp. 209–271 and particularly p. 238.

Included by the thermosetting organic condensation resins of formaldehyde which can be used in the practice of the present invention are, for example, urea type resins, phenol-formaldehyde type resins.

In addition, there can be used melaminethiourea resins, melamine, or urea aldehyde resins, cresol-formaldehyde resins and combinations with other carboxy, hydroxyl, amino and mercapto containing resins, such as polyesters, alkyds and polysulfides.

Some of the vinyl organic prepolymers which can be used to make the polymerizable compositions of the present invention are, for example $CH_2=CH-O-(CH_2-CH_2O)_{n'}-CH=CH_2$, where $n'$ is a positive integer having a value up to about 1000 or higher, multifunctional vinylethers, such as 1,2,3-propane trivinylether, trimethylolpropane trivinylether, prepolymers having the formula,

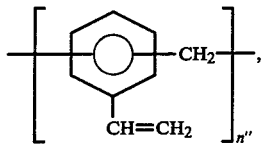

low molecular weight polybutadiene having a viscosity of from 200 to 10,000 centipoises at 25° C., etc. Products resulting from the cure of such compositions can be used as printing inks and other applications typical of thermosetting resins.

A further category of the organic materials which can be used to make the polymerizable compositions are cyclic ethers which are convertible to thermoplastics. Included by such cyclic ethers, are, for example, oxetanes such as 3,3-bis-chloromethyloxetane, alkoxyoxetanes as shown by Schroeter U.S. Pat. No. 3,673,216, assigned to the same assignee as the present invention; oxolanes such as tetrahydrofuran, oxepanes, oxygen containing spiro compounds, trioxane, dioxolane, etc.

In addition to cyclic ethers there are also included cyclic esters such as beta-lactones, for examples propiolactone, cyclic amines, such as 1,3,3-trimethylazetidine and organosilicon cyclics, for example, materials included by the formula,

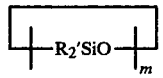

where R′ can be the same or different monovalent organic radical such as methyl or phenyl and m is an integer equal to 3 to 8 inclusive. An example of an organosilicon cyclic is hexamethyl trisiloxane, octamethyl tetrasiloxane, etc. The products made in accordance with the present invention are high molecular weight oils and gums.

In the practice of the invention the alkylaryliodonium salt can be made by the condensation of an arylidosoarylsulfonate with an active hydrogen compound as previously described. Effective results can be achieved by utilizing substantially equal molar amounts of the aryliodosoarylsulfonate with the active hydrogen compound. Temperatures in the range of about −10° C. to 100° C. can be employed. In particular situations, an exothermic reaction can occur requiring the use of external cooling, such as an ice bath. In addition organic solvents, for example, chloroform, dichloromethane, 1,2-dichloroethane, acetone, methylethylketone, chlorobenzene, dioxane, 1,2-dimethoxyethane, nitromethane, etc., and agitation of the mixture such as stirring has been found to facilitate the reaction.

The alkylaryliodonium salts included within formula (1) can be made by a metathesis reaction between the alkylaryliodonium sulfonate salt with an appropriate alkali metal or alkaline earth metal polyfluoro metal or metalloid as previously described. Equal molar amounts of alkylaryliodonium salt and the alkali metal polyfluoro metalloid salt can be used at temperatures in the range of between about −10° C. to 100° C. with agitation of the ingredients. Water or a suitable organic solvent, for example, methylethylketone, acetone, dioxane, acetonitrile, ethanol, ethanol/water, isopropanol, n-butanol, etc., can be used to facilitate reaction. Recovery of the desired alkylaryl iodonium polyfluoro metal or metalloid salt can be achieved by filtration of the resulting alkylaryliodonium salt crystals. Washing of the resulting alkylaryliodonium salt crystals with water is preferred to facilitate the removal of the alkali metal or alkaline earth metal arylsulfonate salt.

Another procedure which can be used to make the alkylaryliodonium salts of the present invention is through the preparation of the already known ylid, followed by acidification with an appropriate acid. This procedure is more particularly shown in "Ylid Chemistry", by A. W. Johnson, Academic Press, New York (1966). The alkylaryliodonium salts within the scope of formula (1) can be made by acidifying the ylid with an appropriate polyfluoro metal or metalloid acid. Substantially equal molar amounts of the ylid polyfluoro metal or metalloid acid is preferred to maximize the desired yield of alkylaryliodonium salt.

There is also provided by the present invention, curable compositions which can be made by blending the aforementioned cationically polymerizable organic material with an effective amount of the alkylaryliodonium salt. A proportion of from about 0.1% to 10% of the alkylaryliodonium salt based on the weight of the cationically polymerizable organic material can be used. In instances where a heat curable composition is desired, a copper compound compatible with the overall heat curable composition, for example a copper salt or copper chelate can be used to catalyze the thermal cure of the curable composition. There can be used from about 0.01 part to about 10 parts of copper compound per part of the alkylaryliodonium salt.

In certain instances, an organic solvent, such as nitromethane, acetonitrile, can be used to facilitate the mixing of various ingredients. The diaryliodonium salts can be formed in situ if desired. In addition, the curable compositions may contain inactive ingredients, such as silica, talc, clay, glass fibers, extenders, hydrated alumina, carbon fibers, process aids, etc., in amounts of up to 500 parts of filler per 100 parts of cationically polymerizable organic material The curable compositions can be applied to such substrates as metal, rubber, plastic, molded parts of films, paper, wood, glass, cloth, concrete, ceramic, etc Some of the applications in which the curable compositions of the present invention can be used are, for example, protective, decorative and insulating coatings, potting compounds, printing inks, sealants, adhesives, molding compounds, wire insulation, textile coatings, laminates, impregnated tapes, varnishes, etc In order that those skilled in the art will be better able to practice the invention, the following examples are given by way of illustration and not by way of limitation.

EXAMPLE 1

There was added 39.2 grams (0.1 mole) of [hydroxy(-tosyloxy)iodo]benzene to a solution of 16.8 grams (0.12 mole) of dimedone in 80 ml of chloroform. An exothermic reaction occurred which was allowed to reach a temperature of 30° C. as a result of the use of an ice water bath and a yellow solution was obtained. The mixture was allowed to stir at room temperature for 1 hour and anhydrous ethyl ether was added to effect the precipitation of product from the solution. The white precipitate was isolated by filtration and washed with anhydrous ethyl ether. Based on method of preparation, there was obtained 41.6 grams, or 81% yield of dimedonylphenyliodonium tosylate. The product had a melting point of 114°–115° C.

A mixture of 16.5 grams (0.023 mole) of dimedonylphenyliodonium tosylate and 6.84 grams (0.032 mole) of potassium hexafluoroarsenate was stirred in 15 ml of water. The metathesis took place gradually. A white solid formed during the 2 hour period the mixture was stirred. The product was recovered by filtering the mixture. Based on method of preparation, there was obtained 12.9 grams, or a 75.5% yield of dimedonylphenyliodonium hexafluoroarsenate having a melting point of 118°–119° C.

EXAMPLE 2

The above procedure was repeated, except that 16.5 grams of the dimedonylphenyliodonium tosylate was mixed with 5.52 grams, or an equal molar amount of potassium hexafluorophosphate. The mixture was stirred for about 2 hours and 50 ml water. In accordance with the procedure of Example 1, there was obtained 11.53 grams or a 74% yield of white solid having a melting point of 116°–118° C. Based on method of preparation the product was dimedonylphenyliodonium hexafluorophosphate.

EXAMPLE 3

Following the procedure of Example 1, a mixture of 9.5 grams of dimedonylphenyliodonium tosylate was mixed with 5 grams or slight molar excess sodium hexafluoroantimonate. The mixture was stirred in 40 ml of methylethyl ketone at 50° C. for ½ to 2 hours. The sodium tosylate salt was removed from the reaction mixture by filtration and the solvent from the resulting filtrate was removed under reduced pressure. There was obtained a brownish oil which solidified when washed with 1,1,1-trichloroethane. The mixture was filtered and a dark tan product was obtained. The product was recrystallized from isopropanol to form 1.3 grams of a white solid having a melting point at 124°–125° C. Based on method of preparation the product was dimedonylphenyliodonium hexafluoroantimonate.

EXAMPLE 4

There were prepared 3% solutions of dimedonylphenyliodonium hexafluoroarsenate, dimedonylphenyliodonium hexafluorophosphate and dimedonylphenyliodonium hexafluoroantimonate in limonene dioxide. The aforementioned salt solutions were found to be definitely stable in the absence of ultraviolet light. The solutions were knife coated onto glass plates to a 1 mil thickness. The glass plates were then irradiated with a GE H3T7 medium pressure mercury arc lamp at a distance of 4 inches. Tack-free times were recorded for each of the three mixtures and the results are as follows:

| Photoinitiator | Tack-Free Time (sec) |
| --- | --- |
| [structure with I$^+$AsF$_6^-$] | 5 |
| [structure with I$^+$PF$_6^-$] | ~60 |

| Photoinitiator | Tack-Free Time (sec) |
| --- | --- |
| 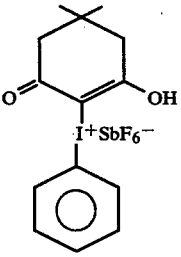 | 5 |

The above results show that the alkylaryliodonium salts of the present invention are valuable photoinitiators for the polymerization of epoxy resins.

EXAMPLE 5

A solution of 98.9% by weight of biscycloaliphatic epoxy resin, CY-179, of the Ceba-Geigy Company, 1% of dimedonylphenyliodonium hexafluoroarsenate, and 0.1% of copper stearate is placed in a General Electric geltime meter. Gel times were recorded at 120° C. It was found that the mixture had a gel time of 19 minutes. A mixture of the aforementioned ingredients free of the alkylaryliodonium salt gave no cure after 5 hours. This result shows that alkylaryliodonium salt of the present invention is a valuable thermal initiator for the polymerization of epoxy resin.

Although the above results are directed to only a few of the very many variables involved in the practice of the present invention, it should be understood that the alkylaryliodonium salts, as shown by formula (1), can be made from the use of a much broader variety of active hydrogen compounds and arylsulfonium salts as shown in the description preceding these examples. In addition, the curable compositions included within the scope of the present invention include a much broader variety of cationically polymerizable organic materials as shown in the description preceding these examples.

What we claim as new and desire to secure by Letters Patent of the United States is:

1. Arylalkyliodonium salts having the formula, $$[R\text{-}I\text{-}Y]^+ MF_d^-$$

where R is a $C_{(6-13)}$ aryl radical, Y is a monovalent aliphatic or cycloaliphatic group selected from

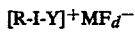

$R^1$ and $R^4$ are selected from hydrogen and $C_{(1-8)}$ alkyl radical $R^2$ and $R^3$ are

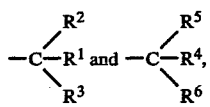

or a mixture of

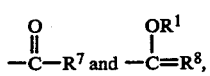

where $R^7$ and $R^8$ are selected from $C_{(1-13)}$ organic radicals which together can form a $C_{(6-13)}$ aromatic radical, $C_{(5-13)}$ heterocyclic radical, or two $C_{(6-13)}$ aryl radicals, a mixture of $C_{(1-8)}$ alkyl and $C_{(6-13)}$ aryl, and a mixture of alkyl and oxyalkyl or alkyl and oxyaryl, and $R^5$ and $R^6$ are monovalent electron withdrawing groups selected from nitrile and a mixture of nitro and $C_{(6-13)}$ aryl M is a metal or metalloid selected from antimony, arsenic, phosphorus and boron, and d is an integer equal to from 4-6 inclusive.

2. An arylalkyliodonium salt having the formula,

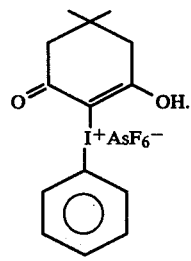

3. An arylalkyliodonium salt having the formula,

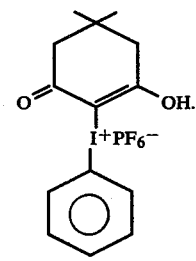

4. An arylalkyliodonium salt having the formula,

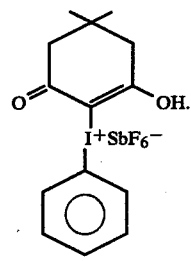

5. A method for making an alkylaryliodonium salt which comprise
   (A) effecting contact between substantially equal molar amounts of an alkylaryliodonium organic sulfonic acid salt having the formula,

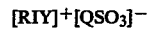

and a polyfluoroalkali metal or alkaline earth metal metalloid salt of the formula,

in the presence of water, or an organic solvent,
   (B) recovering the resulting arylalkylpolyfluoro metalloid iodonium salt from the mixture of (1), and
   (C) washing the resulting arylalkyliodonium salt with a sufficient amount of water to eliminate alkali metal or alkaline earth metal organic sulfonic acid salts from the resulting arylalkyliodonium polyfluoro metalloid iodonium salt,
where R is a $C_{(6-13)}$ aryl radical, Y is a monovalent aliphatic or cycloaliphatic group selected from

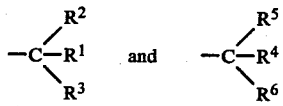

$R^1$ and $R^4$ are selected from hydrogen and $C_{(1-8)}$ alkyl radicals, $R^2$ and $R^3$ are

or a mixture of

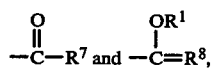

where $R^7$ and $R^8$ are selected from $C_{(1-13)}$ organic radicals which together can form a $C_{(6-13)}$ aromatic radical, $C_{(5-13)}$ heterocyclic radical, or two $C_{(6-13)}$ aryl radicals, a mixture of $C_{(1-8)}$ alkyl and $C_{(6-13)}$ aryl, and a mixture of alkyl and oxyalkyl, or a mixture of alkyl and oxyaryl, and $R^5$ and $R^6$ are monovalent electron withdrawing groups selected from nitrile and a mixture of nitro and $C_{(6-13)}$ aryl, Q is a $C_{(1-13)}$ organic radical, M is a metal or metalloid selected from antimony, arsenic, phosphorus and boron, and d is an integer equal to from 4–6 L inclusive.

6. A method in accordance with claim 5, where the arylalkyliodonium arylsulfonic acid salt is dimedonylphenyliodonium tosylate.

7. A method in accordance with claim 5, where the arylalkyliodonium arylsulfonic acid salt is dimedonyltolyliodonium tosylate.

8. A method in accordance with claim 5, where the alkali metal polyfluoro metalloid salt is potassium hexafluoroarsenate.

9. A method in accordance with claim 5, where the alkali metal polyfluoro metalloid salt is potassium hexafluorophosphate.

10. A method in accordance with claim 5, where the alkali metal polyfluoro metalloid salt is potassium hexafluoroantimonate.

* * * * *